United States Patent
Holloway

(10) Patent No.: US 7,251,619 B2
(45) Date of Patent: Jul. 31, 2007

(54) COMPUTER IMPLEMENTED METHOD, COMPUTER PROGRAM PRODUCT, AND SYSTEM FOR GEM EVALUATION

(75) Inventor: Garry I Holloway, Canterbury (AU)

(73) Assignee: Garry Ian Holloway, Canterbury, Victoria (AU)

( * ) Notice: Subject to any disclaimer, the term of this patent is extended or adjusted under 35 U.S.C. 154(b) by 673 days.

(21) Appl. No.: 09/883,561

(22) Filed: Jun. 18, 2001

(65) Prior Publication Data

US 2002/0052170 A1 May 2, 2002

Related U.S. Application Data

(60) Provisional application No. 60/229,861, filed on Sep. 1, 2000.

(51) Int. Cl.
*G07F 17/30* (2006.01)

(52) U.S. Cl. ............... 705/26; 356/30; 63/32; 705/27

(58) Field of Classification Search ........ 705/26, 705/27; 700/108; 356/30; 63/32
See application file for complete search history.

(56) References Cited

U.S. PATENT DOCUMENTS

| | | | | |
|---|---|---|---|---|
| 4,527,895 A | * | 7/1985 | Rubin | 356/30 |
| 4,647,194 A | | 3/1987 | Shigetomi et al. | 356/30 |
| 5,966,673 A | * | 10/1999 | Shannon, Sr. | 702/35 |
| 6,304,853 B1 | * | 10/2001 | Malnekoff | 705/27 |
| 6,556,883 B2 | * | 4/2003 | Iwayama | 700/108 |
| 6,745,596 B2 | * | 6/2004 | Wueste | 63/32 |

FOREIGN PATENT DOCUMENTS

GB    1416568 A    * 12/1975

OTHER PUBLICATIONS www.tradeshop.com as cited on May 10, 2000 (6 pages).*
www.niceice.com as cited on May 10, 2000 (13 pages).*
Results of study performed in 1999 by the Moscow State University, reported on the following Internet site: www.gemology.ru.

* cited by examiner

*Primary Examiner*—Matthew S. Gart
*Assistant Examiner*—Adam Levine
(74) *Attorney, Agent, or Firm*—Baker & Daniels LLP

(57) ABSTRACT

System and method for providing a gem assessment based upon proportional parameter values relating to the proportions of a gem, such as a diamond. A gem cut quality rating is provided. The system and method are particularly suited for use in an online environment or may be utilized in conjunction with rough diamond analysis instruments in order to provide cutters with greater guidance as to the most appropriate dimensions to cut rough diamonds in order to maximize the yield of a rough diamond and to also produce a diamond of an acceptable grade.

24 Claims, 7 Drawing Sheets

Prior Art

COMPUTER IMPLEMENTED METHOD, COMPUTER PROGRAM PRODUCT, AND SYSTEM FOR GEM EVALUATION

CROSS-REFERENCE TO RELATED APPLICATION

This application is related to and claims the benefit under 35 U.S.C. §119(e) of U.S. Provisional Patent Application Ser. No. 60/229,861, filed Sep. 1, 2000.

FIELD

The present invention relates to the field of gem evaluation and more particularly to the field of diamond evaluation.

BACKGROUND

The cutting of gems such as diamonds is a highly skilled art with many variables that combine to create gems of varying qualities. The laws of physics dictate that, when proportioned correctly, a diamond will reflect back a maximum amount of the light that enters the stone. Because proportions are such a critical element in the diamond's beauty, the ideal cut has become identified as the standard of diamond beauty. In this regard FIG. 1 illustrates the various parameters that define the cut of a diamond, including table, crown and pavilion angles, culet and girdle.

Most of a diamond's life and sparkle comes from its cut. Diamonds are often cut to retain weight, which results in light leaking out the back of the diamond, and also a dull drab diamond with a smaller diameter.

In 1919, Marcel Tolkowsky wrote a Masters thesis on the ideal proportions for round diamonds. The proportions designated by Tolkowsky's have generally been considered as well chosen and have been the benchmark in the industry for the past 80 years. The target set by Tolkowsky was of a diamond with crown angle of 34.5°, pavilion 40.75° and table of 53%.

However, Tolkowsky's ideal design has led to the industry developing the have been used to develop tolerances of an "ideal cut". This has been an incorrect application of Tolkowsky's ideal, as not all diamonds within the designated tolerances in fact could be described as "ideal". Further, recent research has shown that there are diamonds outside of the proportions indicated by Tolkowsky that are equally or even more beautiful.

Cut grading systems were developed in order to assist in classifying high quality cuts from lesser quality cuts. However, as existing cut grading systems are generally based on the developed tolerances, they are inadequate. Further such systems are feature oriented in that they provide a numerical grading for the diamond. Laboratories that provide such a numerical grading take the worst scoring feature and assign that score as a cut grade. This process ignores the complex interrelationship of facets as light reflects and refracts on its passage through a diamond. A diamond with a slight deviation on each of these measures can rate as ideal even though the performance is only fair. Equally some deviations for Tolkowsky's proportions can compensate for other undesirable deviations in other factors.

It is therefore apparent that large discrepancies can exist in the way institutional "tolerances" are applied to a single "ideal cut". Further, today's grading systems are not flexible enough to take account of different proportion preferences of individuals or geographic markets. Many consumers, particularly sophisticated consumers, expect more of cut grading systems. There is therefore a need for a more flexible and accurate grading system.

It is also apparent that there are many variables in assessing the quality and beauty of a diamond, and that, particularly from the lay person's point of view, it can be a difficult decision choosing the right diamond. There is therefore a need for a simplified gem assessment system and method.

In addition, there are numerous diamond traders around the world selling diamonds of varying quality. For a person, particularly one not experienced in the gem trade, it can be a difficult process evaluating diamonds and judging their appearance based upon the cut factors listed by the traders. Also, it can be time-consuming process evaluating diamonds from the various traders.

There is therefore also a need for an improved system for evaluating gems of multiple remote traders.

The present invention seeks to overcome or alleviate at least one of the problems of the prior art.

SUMMARY OF THE INVENTION

According to a first aspect, the present invention provides, in an online environment, a method of providing a user with a gem assessment, the method including the steps of receiving a plurality of proportional parameter values from the user relating to the proportions of the gem; obtaining a plurality of aesthetic parameter values based upon the received proportional parameter values; and providing a gem rating based upon the plurality of aesthetic parameter values.

According to a further aspect, the present invention provides, a computer program product including a computer usable medium having computer readable program code and computer readable system code embodied on said medium for providing a user with a read-only copy of a document electronically available over an on-line network, said computer program product further including computer readable code within said computer usable medium for receiving a plurality of proportional parameter values from the user relating to the proportions of the gem; obtaining a plurality of aesthetic parameter values based upon the received proportional parameter values; and providing a gem rating based upon the plurality of aesthetic parameter values.

The essence of the invention lies in the ability to provide a grading relating to aesthetic characteristics of a gem, particularly a diamond, based upon its proportions. The invention hence is able to provide a description of the visual appearance of gems in simple terms, even though the variables and issues involved are enormously complex.

In particular, the invention may be advantageously implemented in an on-line environment, such as the Internet, or via an in-situ software program, in order to provide an advisory service in relation to the aesthetic characteristics of a gem cut when information relating to the gem's proportions are provided.

Another benefit of the present invention is that by providing the software in an interface with rough diamond analyzers, it will not only improve diamond beauty, but it will give flexibility to cutters to increase yields.

BRIEF DESCRIPTION OF THE DRAWINGS

An illustrative embodiment of the invention will now be described with reference to the accompanying figures, in which.

DETAILED DESCRIPTION

Figure 1:
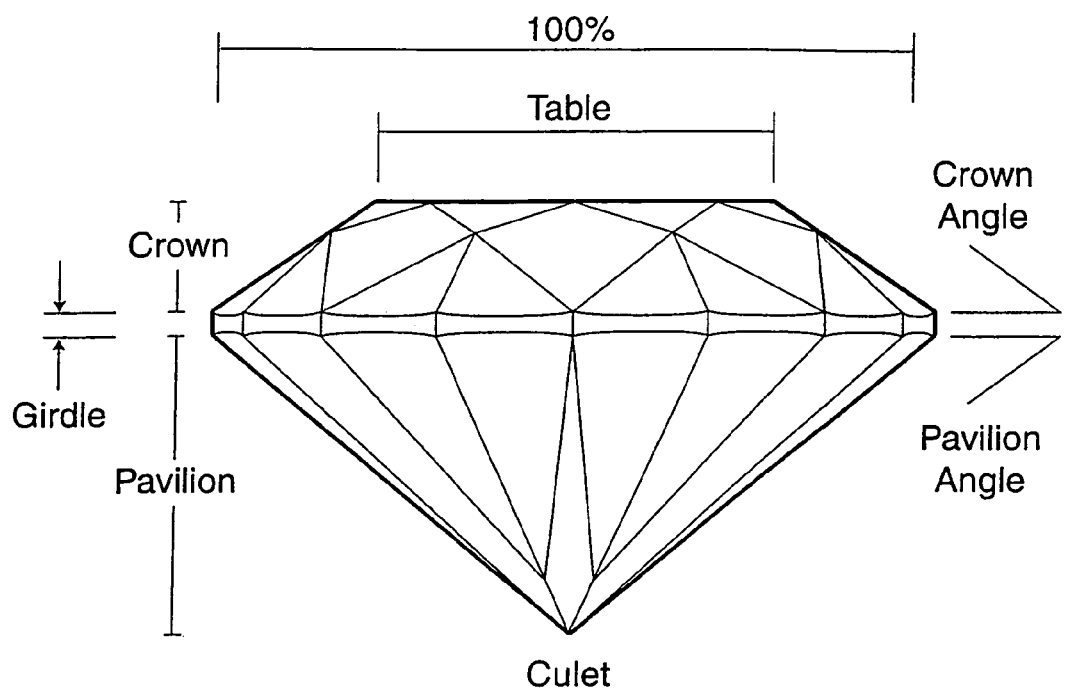
FIG. 1 illustrates the various parameters of a diamond.

According to a first aspect of the present invention, a system has been developed whereby the various cuts of a diamond are defined in terms of individual user preferences. That is, the various cuts of a diamond are assessed according to factors that characterize the beauty and desirability of the diamond.

In this regard, three factors are commonly used to assess the beauty of a diamond being brilliance, fire or dispersion and scintillation.

Brilliance

Brilliance is generally considered to be the most important feature when considering diamond beauty. If brilliance is compromised then the effectiveness of a diamond's fire and scintillation is also reduced. Brilliance is often related to proportions that reduce light loss from the pavilion of a diamond. The understanding of brilliance must include the directions in which light travels to an observer and the source and type of light used in any analysis.

Fire or Dispersion

Fire is the term used to describe the spectral separation or dispersion of white light into rainbow flashes. Fire is generally considered to be enhanced with steeper crown angles and smaller tables.

Scintillation

Scintillation is perhaps the least clearly defined visual feature in diamond appearance. One definition is "a pleasing visual balance in the spread of clearly defined and well spread dark and light areas that flash on and off as a light source, the stone or the observer's position change". The dark areas should be a small component of the overall stone's face up appearance with a head shadow of 21 degrees. Scintillation is dependent on the type of lighting, the observer's physical presence and the diamond itself. It is more personal than brilliance and fire, because the more of these two features the better, whereas the ideal amount of blackness and contrast is in the eye of the beholder.

Spread

A further desirability factor that may be considered in the system according to the present invention is "diameter spread". That diamonds of the same weight but different proportions can appear bigger or smaller is often referred to as "spread". This factor, however, is an economic or desirability factor rather than a beauty factor.

According to a first embodiment of the invention, the system is fed various cut features of a diamond, such as crown and pavilion angles and table percentage. Based upon the actual values, input, the system produces a simple description of the visual appearance of the diamond in terms of the beauty factors of the diamond. Therefore, in this way, rather than just providing a numeric grade, the customer is provided with a definition from which the individual is able to form their own opinion, based upon personal or regional taste.

In this regard, the present invention uses a look-up table or the like which matches diamonds having particular cut features with appropriate beauty factors.

In this regard, according to the first embodiment of the invention, weightings are given to all of the factors being considered, such as:

| FACTOR | WEIGHTING |
|---|---|
| Brilliance | 0 to 4 |
| Fire | 0 to 2 |
| Scintillation | 0 to 2 |
| Spread | 0 to 2 |
| TOTAL SCORE | 0 to 10 |

From these weightings it is apparent that the system is based upon holistic information, rather than unrelated individual features, and that the feature considered most important in assessing diamond beauty is brilliance.

In order to apply the holistic information to particular diamond cuts, a cross correlation between the various cuts and the holistic information needs to be established. This may be achieved in various ways, such as by studying actual diamonds in order to calculate penalty values. However, it is more efficiently performed using virtual diamond analysis, as this eliminates problems with variation in color, clarity and the minor facet groups. Examples of software programs that may be utilised include Diamcalc™, Firescope™ and Gilbertson-Scope. These software packages are available from OctoNus Software Limited, a company founded by Moscow State University, Russia.

Such software programs may be used to develop charts of diamond images of the most commonly encountered diamond proportions. For the present example, the range chosen was for table sizes between 54% and 65% on a grid of the pavilion angles between 39.5° and 43° in 0.5° graduations and steps of one degree for crown angles between 28° and 40°.

The Firescope™ instrument, as distinct from the Firescope™ software, enables the light return of real diamonds to be studied and appropriate weightings given in regard to brilliance. In this regard, using the virtual Firescope software, it has been found that consumers show a preference for diamonds with a strong red light return and a black eight star pattern. Therefore, using the Firescope™ software, diamonds displaying this feature were given a good brilliance rating.

From this analysis it became apparent that as table size increases, the black stars in the stones identified as falling within the recommended areas are seen to become thinner and less well defined. Also, it became apparent that variations in pavilion angles could be compensated for by a larger opposing variation in crown angles. This resulted in a broader range of proportions than the Tolkowsky proportions that yielded beautiful diamonds.

Therefore, such subjective analysis was applied to all the virtual diamonds in the grid patterns using the Diamcalc software tools, predominantly from a "face up" position, and each given an appropriate brilliance score of zero to four, whereby the lower the score, the better the brilliance.

In order to verify the results, cross correlation was performed by comparing diamonds with the same score from different areas on each grid, and those from other table size grids. Finally results were confirmed by showing actual diamonds with known proportions to numerous observers in various lighting environments.

Figure 2:
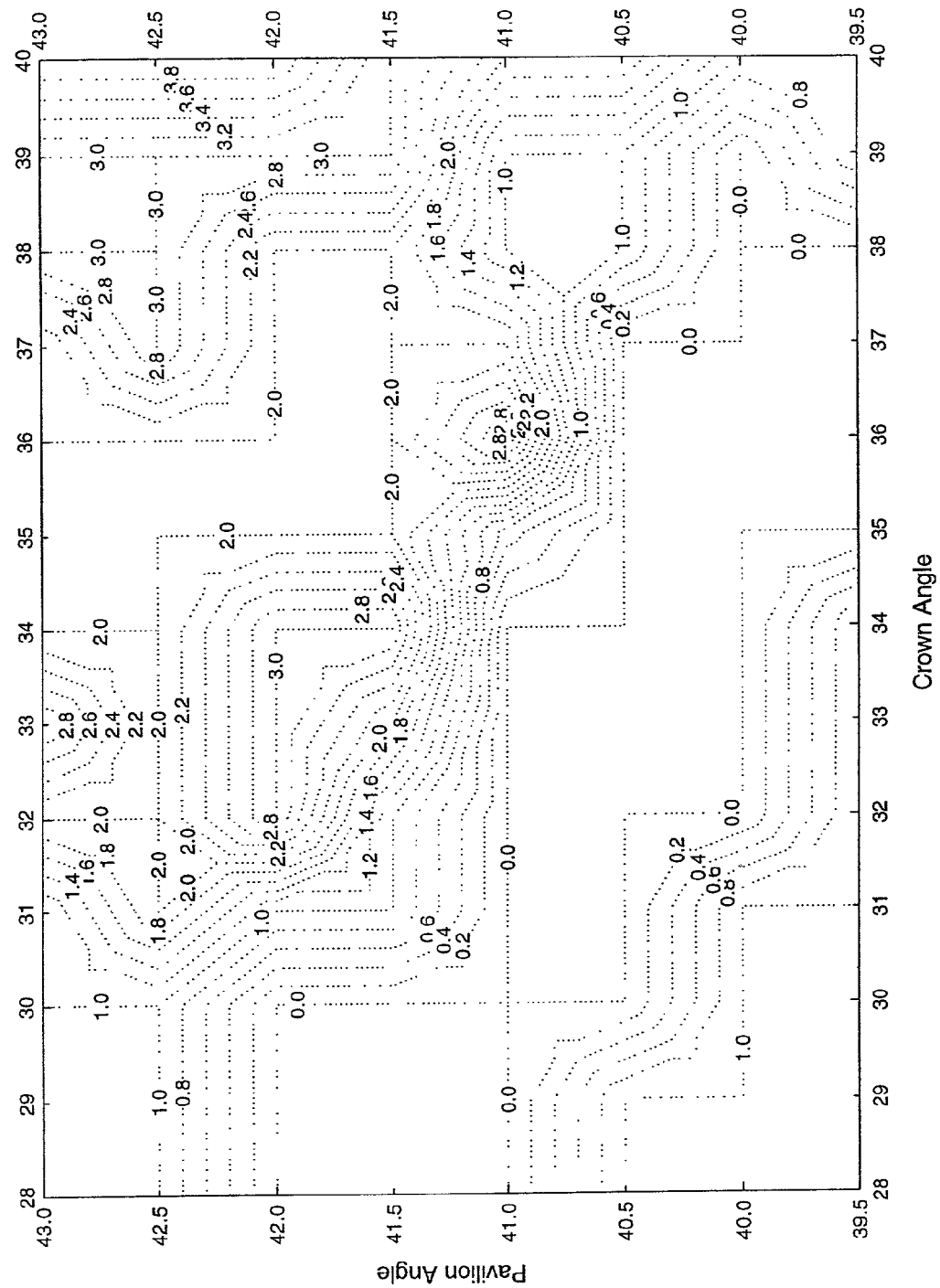
FIG. 2 illustrates comparative brilliance scores estimated for diamonds with crown angles from 28° to 40°, pavilion angles from 39.5° to 43.0° and table of 56%.

FIG. 2 illustrates graphically the comparative brilliance scores from one of the several charts devised for diamonds with varying crown and pavilion angles, and with a table size of 56%. These results are based upon extensive research into consumer preferences and desired characteristics. It is therefore to be appreciated that these results are subjective and may be altered in order to cater for user preferences in particular brilliance characteristics.

Figure 3:
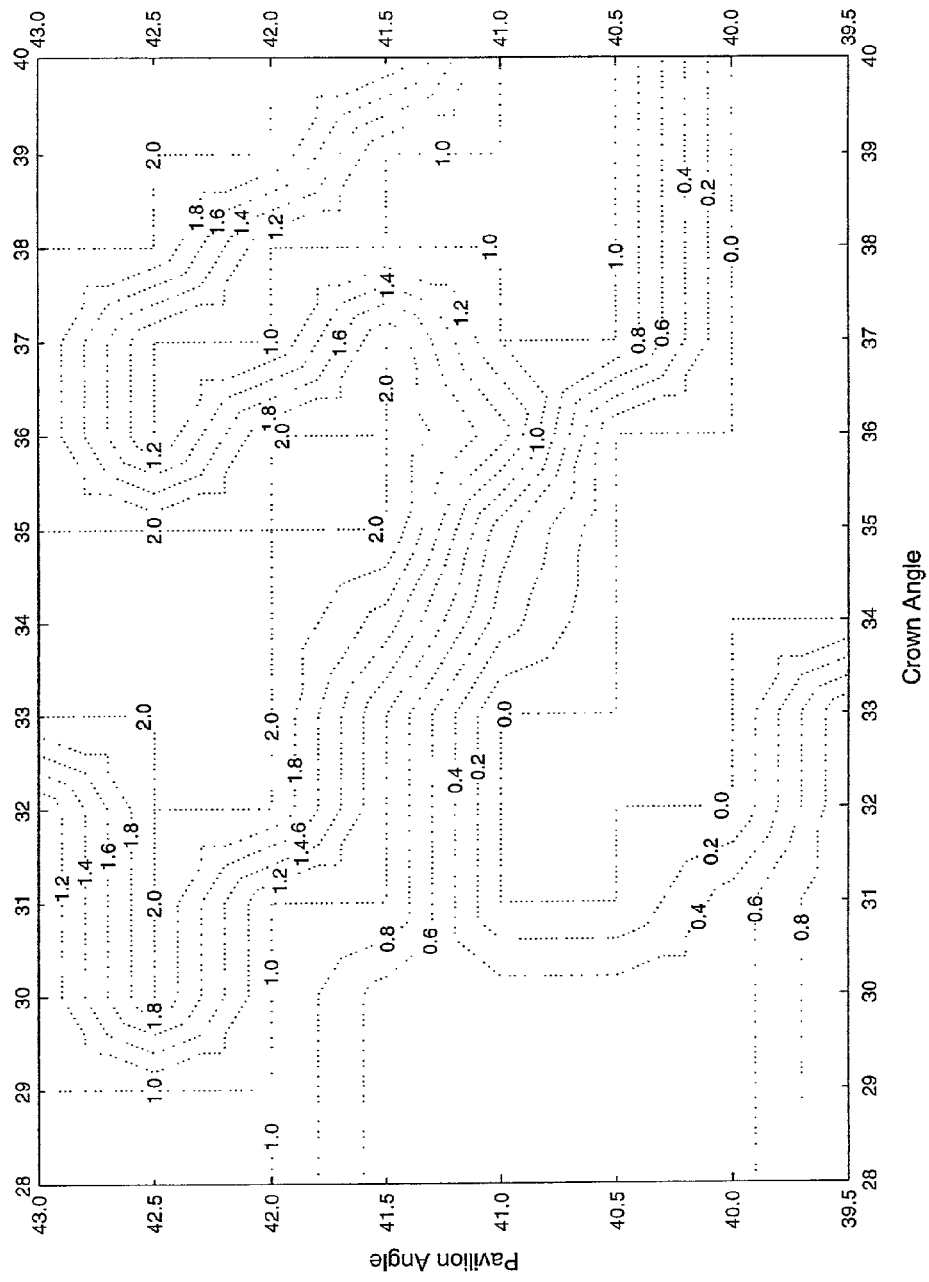
FIG. 3 illustrates comparative fire scores estimated for diamonds with crown angles from 28° to 40°, pavilion angles from 39.5° to 43.0° and table of 56%.

FIG. 3 similarly illustrates graphically the comparative fire scores devised for diamonds with varying crown and pavilion angles, and with a table size of 56%. These results were also based upon extensive research of consumer preferences and desired characteristics, and also aided by the use of software, such as DiamCalc, that enables ray path analysis to be performed.

Figure 4:
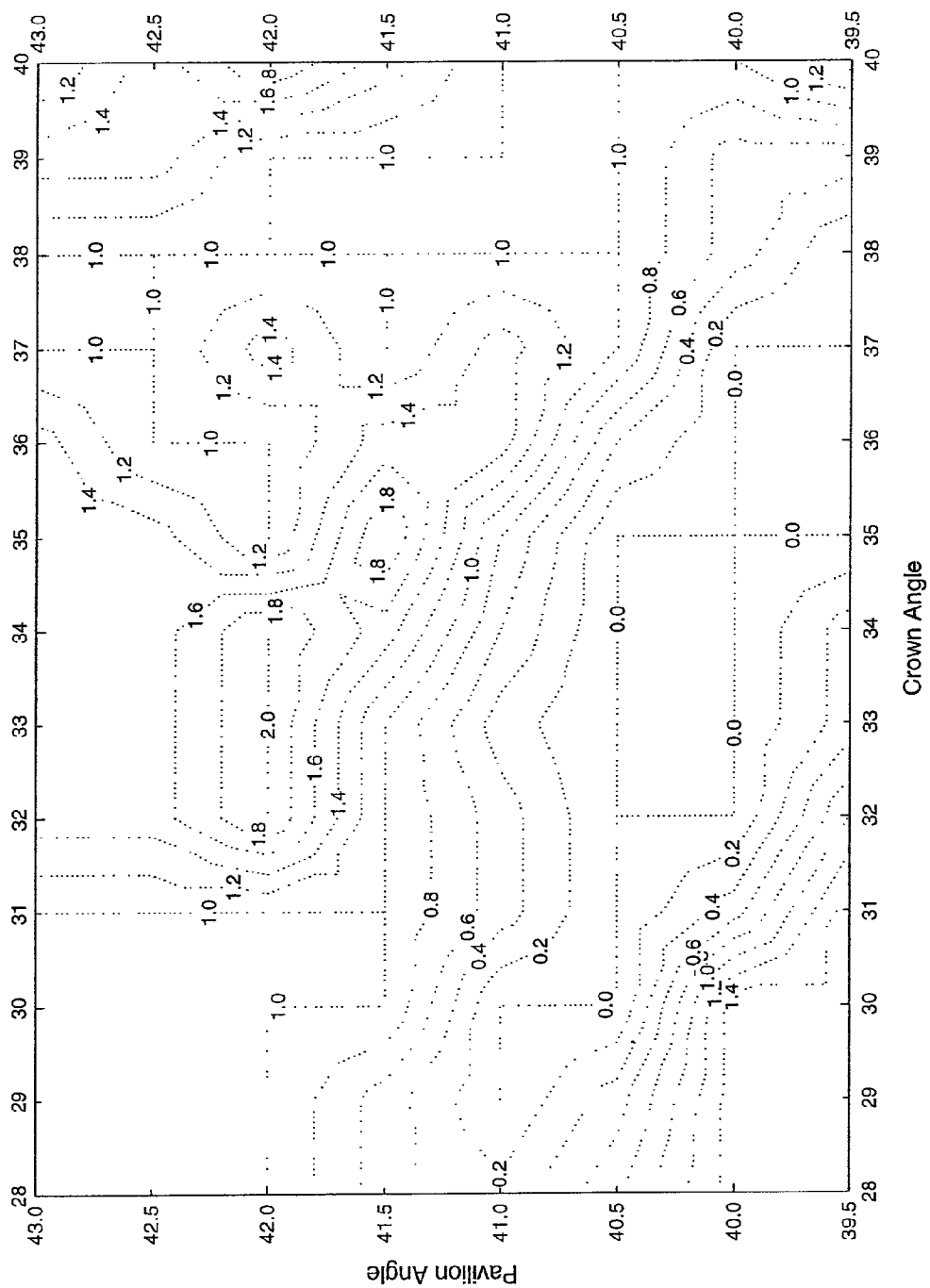
FIG. 4 illustrates comparative scintillation scores estimated for diamonds with crown angles from 28° to 40°, pavilion angles from 39.5° to 43.0° and table of 56%.

Further, FIG. 4 illustrates graphically the comparative scintillation scores devised for diamonds with varying crown and pavilion angles, and with a table size of 56%. Scintillation is dependent on the type of lighting the observer's physical presence and the diamond itself. The scores devised in FIG. 4 were based upon charts that used a relative head size of 150 mm (6 inches) from a distance of 407 mm (16.3 inches) which is blocking 21 degrees of the 180 degrees of available light source above the plane of the girdle.

Figure 5:
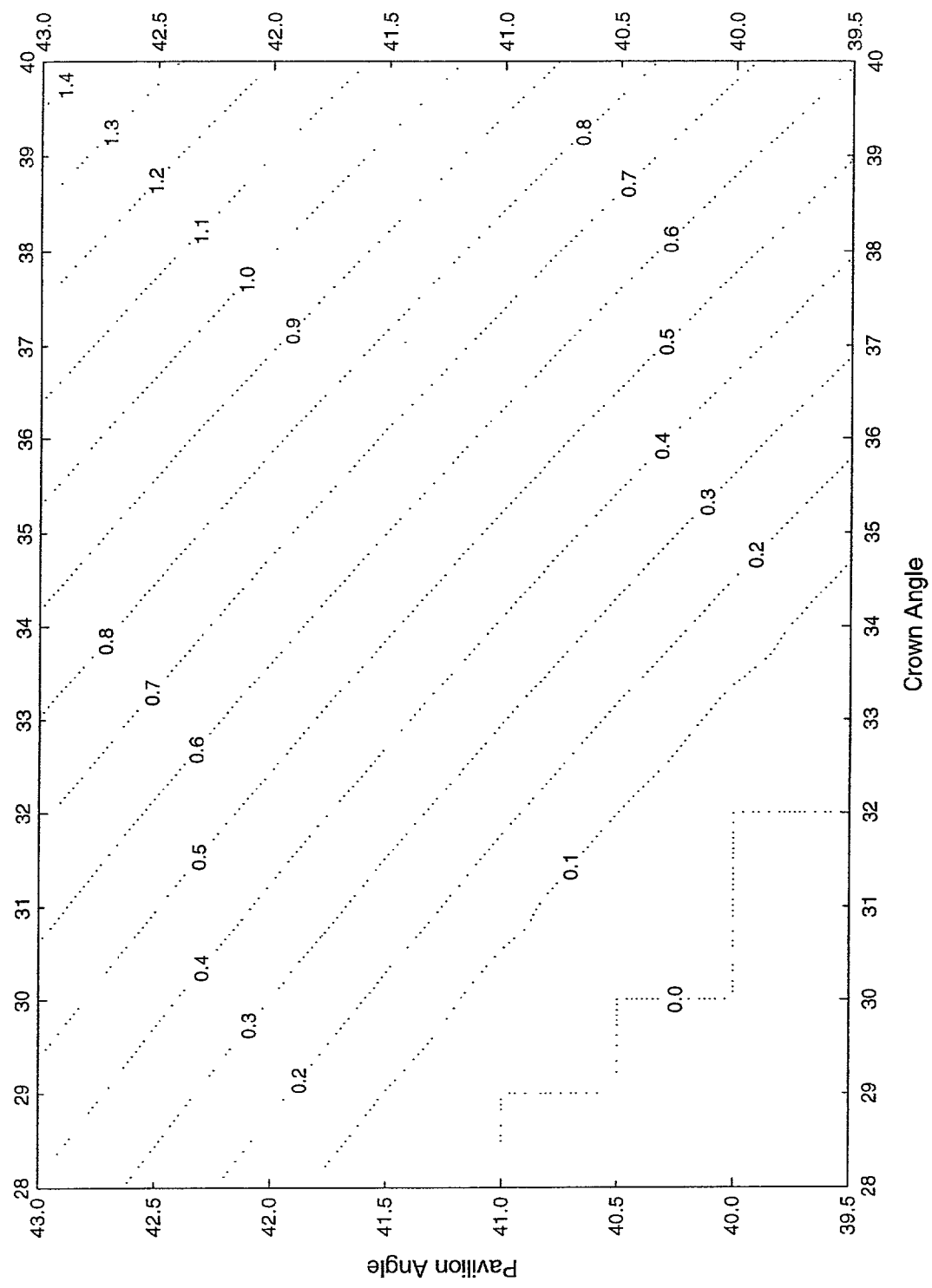
FIG. 5 illustrates comparative spread scores estimated for diamonds with crown angles from 28° to 40° pavilion angles from 39.5° to 43.0° and table of 56%, girdle of 2% and culet of 0%.
Figure 6:
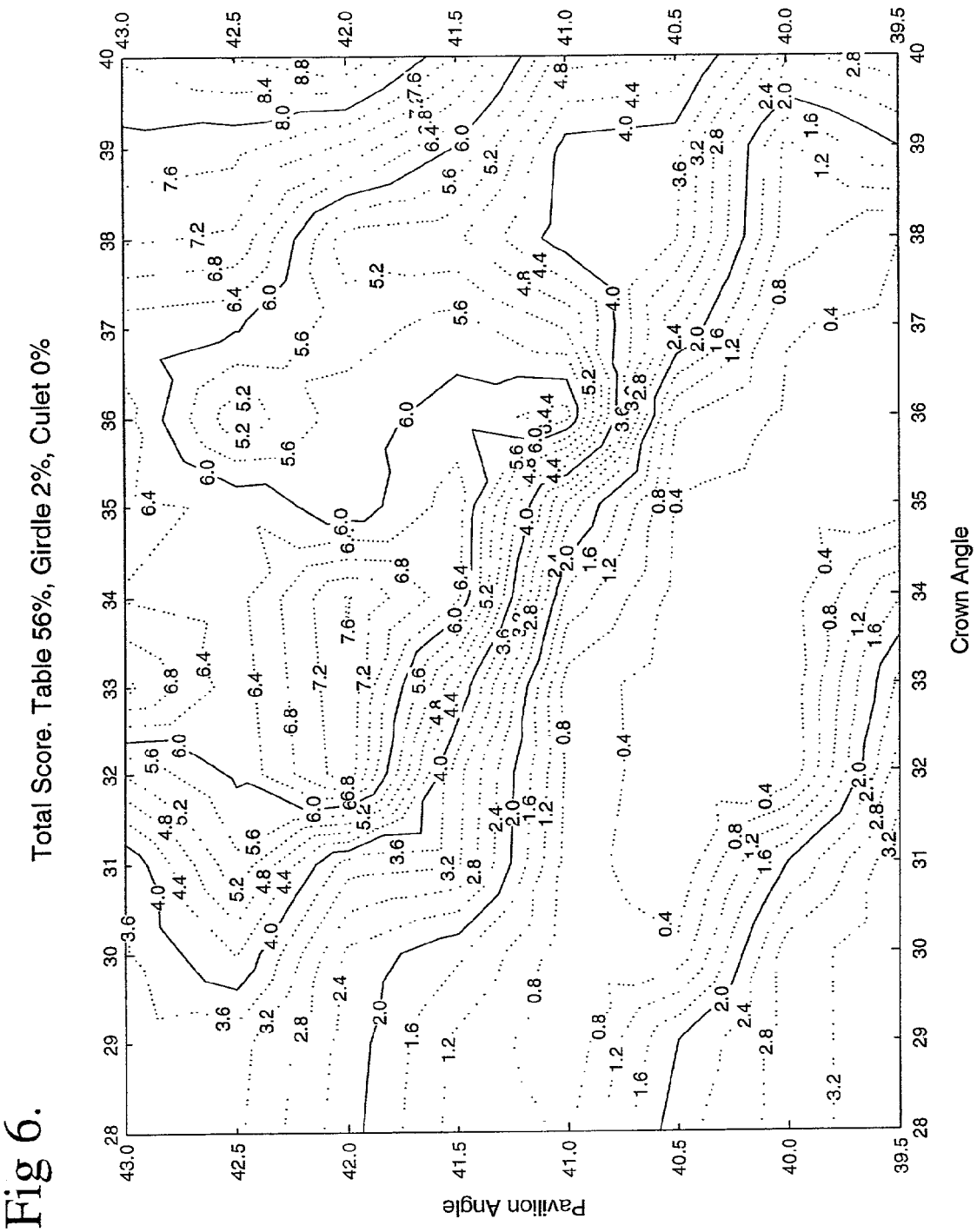
FIG. 6 illustrates a total score chart estimated for diamonds with crown angles from 28° to 40°, pavilion angles from 39.5° to 43.0° and table of 56%, girdle of 2% and culet of 0%.
Figure 7:
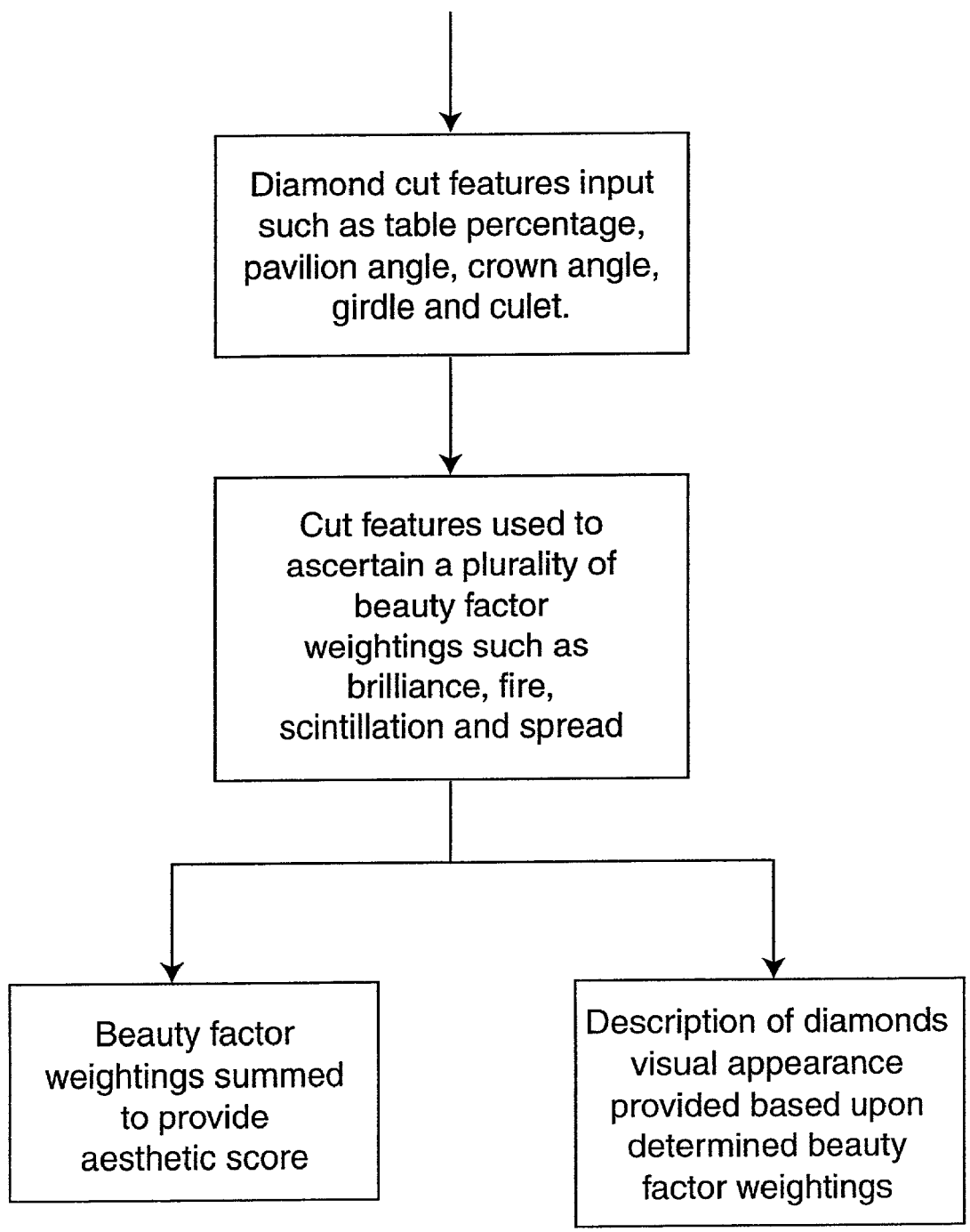
FIG. 7 illustrates a flow chart according to an embodiment of the invention.

FIG. 5 illustrates comparative spread scores for diamonds with a 56% table. The spread scores were devised by taking into account diamond weight, depth percentage as well as actual subjective beauty.

It is to be appreciated that the results of FIGS. 2, 3 and 4 and 5 were produced essentially by considering the face up viewing position of the diamond because of the economic importance of this position. This is because most diamond sales are made by observing diamonds from a face up view. Nevertheless, this is not an essential component of the invention, and the model used in developing weightings could equally be based upon other viewing positions, such as oblique positions.

Although the aesthetic penalties in relation to brilliance, fire, scintillation and diameter spread are the most preferred qualities to account for, penalties or adjustments in relation to other aesthetic qualities may also be taken into account in the overall model.

Vertical Spread Adjustment

For example, in another embodiment of the invention, a further aesthetic feature of diamonds that may be taken into consideration in calculating a penalty weighting is vertical spread. Vertical spread is different to diameter spread. It is an issue that consumers raise from time to time and is the amount of diamond that can be seen projecting above a setting. Generally vertical spread comes at the cost of reducing "diameter spread". For example, a somewhat subjective allowance for this factor could be a 20% weighing in the spread factor for stones with steep crowns and small tables.

Table Size Adjustments

Generally, the best looking diamonds have table sizes of 53% to 60% (measured as a percentage of the diameter of the diamond). Diamonds with table sizes that are too large or too small have some impact on diamond beauty. Hence, it is preferable for a penalty factor for such table sizes to be applied to each of the beauty factors as follows:

| Table Size | Too Small | Optimum | Too Large |
|---|---|---|---|
| | ←50%–53% | 53%–60% | 60%–65%→ |
| Brilliance Score | ←1.0 to 0 | 0 | 0 to 1.0→ |
| | ←50%–53% | 53%–58% | 58%–65%→ |
| Fire Score | ←0.5 to 0 | 0 | 0 to 1.0→ |
| Scintillation | ←0.5 to 0 | 0 | 0 to 1.0→ |

The arrows indicate that penalties continue below 50% and above 65% table sizes. Hence, a diamond with a table size of 62.5% has scores of brilliance of 0.5, fire 0.643 and scintillation 0.643 giving a total penalty of 1.786. This means it is possible for a diamond with this size table to score an excellent grade.

Girdle Adjustment

In a still further embodiment of the invention, a further aesthetic feature that may be taken into consideration in calculating penalty weightings is an adjustment for the girdle thickness. Ray path analysis shows that polished girdles refract some light back above the girdle in the same way as other facets. However, for this to occur, it would require a diamond to be set with an exposed girdle. Nevertheless, on balance, thick girdles result in less light return and can look like inclusions, especially if bruted rather than faceted. Thick, very thick and extremely thick girdles weigh much more but are one of the most effective ways to maintain yield without sacrificing beauty. Diamonds with extremely thin and very thin girdles are given a penalty because of the undesirable risk of damage. It should be noted that the spread factor provides an additional penalty for a diamond with an overly thick girdle.

With these considerations in mind, the following penalty deduction for overly thin and overly thick girdles:

| 0% | 1% | 2% | 3% | 4% | 5% | 6% | 7% | 8% | 9% | 10% | 0.5 to <0 |
|---|---|---|---|---|---|---|---|---|---|---|---|
| <1.0 → | | | | | | | | | | | |

Hence in the girdle range between 4% and 10%, the penalty is between zero to one on a continuum, and the continuum extends further for excessively large girdles.

Fish Eye Adjustment

According to a further embodiment of the invention, an adjustment may be made for fish-eyes. A fish-eye appears as a circular inclusion and is a reflection of the girdle on the opposite side. Fish eyes are most apparent if the pavilion is shallow and the table is large or a combination of the two. Fish eyes can be seen in diamonds with a 41° pavilion and 72.2% table and at 390 pavilion and 58.4% table and any proportions in between, with no tilt. Also, as the table gets 1% bigger, a 1% larger fish-eye is apparent. Nevertheless, a near fish-eye may be considered desirable because the stone will have an excellent spread.

In relation to the weightings given to diamonds evaluated using the present invention, a score of 1 is added for 0% on a sliding scale where 5% is given 0.2.

As fish-eyes are generally an undesirable trait, an automated comment in relation to the fish-eye should be generated for appropriate stones. For example:

| Percentage | Comment |
| --- | --- |
| <1% or less | Do not buy this diamond under any circumstances, as it is a fisheye. |
| >1% to <3% | This diamond is almost a fisheye. |
| >3% to 5% | A small amount of tilt will show a fisheye under the table of this diamond. |

The percentages in this table refer to the ABC Page-Thiesen Diamond Grading scheme, although any suitable grading system may be utilised.

Culet Adjustment

A large culet on a diamond allows a small amount of light loss, but more importantly mars the appearance. In this regard, a culet often appears as a black inclusion.

In order to account for this problem, if a culet size is smaller than 1%, no penalty is added. However, for culet sizes above 1%, a penalty is added on a sliding scale, with a 5% culet size adding a penalty of 0.8.

Advisory System

With all required weightings and adjustments determined, these calculations may then be utilised in a user-friendly system for evaluating a diamond. In this regard, the system would operate by requiring a user to directly input the cut parameters of a diamond of interest, or via an interface with a proportion measuring device or other proportion data processing means.

Based upon the input parameters, the system will then match these parameters with the relevant tables of brilliance, fire, scintillation and spread ratings and other applicable adjustments in order to obtain an appropriate weighting for each factor, as well as a total score. An overall comment may also be provided.

For example, for a diamond having a table of 56%, a pavilion angle of 42°, a crown angle of 31°, a girdle of 2% and a culet of 0%, the diamond will obtain a weighting of 1.0 for brilliance, 1.0 for fire, 1.0 for scintillation and about 0.46 for spread. This diamond will therefore have an overall penalty of 3.46. It is to be appreciated that the worst looking diamond would be rated as ten or more. A score of zero would be extremely uncommon, and in fact most popular Tolkowsky proportioned diamonds would score around one. It is hence apparent that this penalty is based upon aesthetic principles and is therefore likely to have more meaning to a lay person.

In addition to the numeric aesthetic penalty rating, it is possible to provide the user with a descriptive assessment of the diamond based upon the diamond cut parameters and/or the penalty weightings given for the aesthetic parameters of brilliance, fire, scintillation and spread. Therefore, in simple words the system can describe how each diamond will most likely look to a buyer in a jewelry store lighting environment for each of the above parameters.

For example, it is possible for the advisory system to recognise three distinct types of diamond with optimum beauty, being Tolkowsky's Ideal Cut (TIC), Brilliant Ideal Cuts (BIC) and Fiery Ideal Cuts (FIC). Brilliant Ideal Cuts return the most light and tend to have the largest spread for the same weight. Fiery Ideal Cuts have more fire or spectral colour and appear to have more facets and scintillation. An FIC is a cut with a steep crown angle in order to increase fire or dispersion, while having a slight reduction in pavilion angle to maintain optimum dispersion. A BIC on the other hand is one with a shallower crown angle and slightly deeper pavilion in order to optimize brilliance. The TIC range combines a balance of fire and brilliance. BIC diamonds tend to weigh less and FIC diamonds weigh more for the same diameter spread.

Therefore, when one of these stones is recognised, the system can include a statement in the assessment, such as:

"This stone exhibits characteristics of a TIC/BIC/FIC".

In this regard, BIC, TIC and FIC characteristics are only given for diamonds in the excellent range (ie less than 2) and with the following crown angles:

| Crown Angle | Diamond Type |
| --- | --- |
| less than 32.5° | BIC |
| more than 35.5° | FIC |
| between 32.5° and 35.5° | TIC |

The system can also provide an assessment based upon each feature being assessed. For example:

Brilliance
0 This diamond has ideal brilliance
1 This diamond has very good brilliance
2 This diamond has good brilliance
3 This diamond has fair brilliance
4 This diamond has poor brilliance
Fire or Dispersion
0 is very firey
1 has good fire
Scintillation
0 and has excellent scintillation
1 and has good scintillation
2 and has poor scintillation
Spread
0 It has a very good "spread" or large diameter for its weight
1 It has a reasonable diameter or "spread" for its weight
2 It is deeply cut and has a poor "spread" or diameter for its weight
Symmetry
0 The symmetry is excellent
0.5 The symmetry is good
1 The symmetry is poor
Polish
0 and the polish is excellent
0.5 and the polish is good
1 and the polish is poor
Girdle Thickness
0 with a medium girdle (very good)
0.5 with a very thin girdle (can chip)
0.5 with a thicker than ideal girdle, so it weights about x % more than if it had a thinner girdle
0.5 this diamond has an extremely thin girdle that is prone to chipping, but the spread is bigger than you would expect
1 this diamond will lose some brilliance through its extremely thick girdle, it weighs about xx% more than it should The present invention therefore provides a system able to furnish a description of the visual appearance of diamonds in simple terms, even though the variables and issues involved are enormously complex. That is, the present invention is able to turn the numerical cut grades into a benefit based rating that defines the cut of a diamond in ways that individual preferences can be identified and satisfied.

In particular the system aids both novice consumers and experienced buyers in selecting unseen diamonds, as if each diamond were lined up side by side.

In fact, in a further embodiment of the invention, where the present advisory system is provided over the Internet, a database could be formed by having a number of traders upload proportions of their diamonds that are for sale. The proportions would preferably be determined using proportion measuring devices, such as those manufactured by Sarin Technologies and Ogi Corporation. For example, Sarin Technologies market a desk-top measurement device that takes a series of 64 pictures of a rotating diamond and measure all its angles and proportions digitally.

Potential customers could then obtain reports using the advisory system in relation to these diamonds, based upon the proportion information, and also view virtual models of the diamonds, created from the proportion information by using virtual modeling tools, like Diamcalc.

In a further embodiment of the invention, proportion measuring devices are used to model every facet of a diamond making it then possible to account for symmetry and other faceting variations and defects, which are then able to be included in the advisory system. This would then enable a virtual image to be generated. Alternatively, the image displayed to the user may be a digital photograph of the appropriate diamond.

Therefore, in addition to the user being given an aesthetic grading and appropriate comment on the diamond, an equivalent image of the diamond may be displayed before the user together with details relating to the relevant trader, such as a hot-link to the trader's site.

The present invention may also be advantageously used in overcoming the problems in existing grading systems, which include inadequate cuts within the "top grades" and exclude other diamonds with favourable combinations of rejected proportions. Thus current systems unfortunately leads cutters to cut for grades and attract healthy margins, as compared to cutting for beauty. That is, diamond cutters will generally cut a diamond within the recognised tolerances of an "ideal cut" which weighs the most, but which typically is dull and drab, as they make more money by cutting deeper, heavier diamonds, that leave a little more weight on the crown and pavilion, even though in actuality, these are not the more beautiful diamonds.

The present invention, however, may be used to redress this problem, in that the cut advisory system may be programmed into rough diamond analysis instruments. This will provide cutters with greater guidance as to the most appropriate dimensions to cut rough diamonds in order to maximise the yield of a rough diamond and to also produce a diamond of an acceptable grade.

Variations and additions are possible within the general inventive concept as will be apparent to those skilled in the art.

I claim:

1. A computer implemented method of providing a user with an assessment of a gemstone having a cut shape, the method including the steps of:
   a computer receiving at least three objective parameter values from the user relating to measured physical proportions of the gemstone, said values selected from the group comprising depth percentage, table percentage, crown angle, crown percentage, pavilion angle, pavilion percentage, culet percentage, girdle thickness, or other analogous physical proportion parameters applicable to the cut shape of the gemstone;
   the computer determining attribute values for a plurality of attributes of the gemstone contributing to visual appeal, including one or more of the following: brilliance, fire, scintillation, and diameter spread;
   wherein each said attribute value is determined by:
      selecting at least three of the received objective parameter values; and
      combining the selected objective parameter values to determine the said attribute value on the basis of predetermined consumer preferences that have been established taking into account the effect, upon the corresponding attribute contributing to visual appeal, of an inter-relationship amongst all of the selected objective parameter values;
   wherein the step of determining includes retrieving said values of attributes contributing to visual appeal from one or more lookup tables indexed by the selected at least three objective parameter values;
   the computer establishing a rating value of the gemstone based upon said values of attributes contributing to visual appeal; and
   the computer providing to the user an assessment of the aesthetic characteristics of the gemstone relative to said predetermined consumer preferences based upon said rating value and/or said values of attributes contributing to visual appeal.

2. Method of claim 1 wherein the step of establishing a rating value includes applying an adjustment to one or more of the values of attributes contributing to visual appeal and/or the racing value in accordance with one or more of the following:
   (i) vertical spread;
   (ii) table size;
   (iii) girdle thickness;
   (iv) culet size;
   (v) half facets;
   (vi) symmetry;
   (vii) polish.

3. Method of claim 1 wherein the gemstone assessment includes a description of the visual appearance of the gemstone based upon the determined values of attributes contributing to visual appeal and/or the established rating value.

4. Method according to claim 1 wherein the gemstone is a diamond.

5. Method of claim 1 wherein entries in the lookup tables are predetermined values computed using a computer software program for performing virtual diamond analysis.

6. Method of claim 1 wherein entries in the lookup tables are predetermined values obtained by analyzing actual diamonds.

7. Method of claim 1 wherein the step of determining includes computing said values of attributes contributing to visual appeal from a virtual model of a diamond corresponding with the received objective parameter values using a computer software program for performing virtual diamond analysis.

8. Method of claim 1 wherein the rating value is established by summing the values of attributes contributing to visual appeal.

9. Method of claim 1 wherein the gemstone assessment includes a numerical value corresponding with the rating value.

10. Method of claim 1 wherein said objective parameter values are received electronically over a telecommunications network link.

11. Method of claim 10 wherein the telecommunications network is the internet.

12. Method of claim 1 wherein establishing the rating value includes applying a corresponding numerical weighting to each of said values of attributes contributing to visual appeal, and summing the weighted attribute values.

13. Computer program product including a computer usable medium having computer readable program code embodied on said medium for providing a user with an assessment of a gemstone having a cut shape, said computer program product further including computer readable code within said computer usable medium for:

receiving at least three objective parameter values from the user relating to measured physical proportions of the gemstone, said values selected from the group comprising depth percentage, table percentage, crown angle, crown percentage, pavilion angle, pavilion percentage, culet percentage, girdle thickness, or other analogous physical proportion parameters applicable to the cut shape of the gemstone;

determining attribute values for a plurality of attributes of the gemstone contributing to visual appeal, including one or more of the following: brilliance, fire, scintillation, and diameter spread;

wherein each said attribute value is determined by:
  selecting at least three of the received objective parameter values, and
  combining the selected objective parameter values to determine the said attribute value on the basis of predetermined consumer preferences that have been established taking into account the effect, upon the corresponding attribute contributing to visual appeal, of an inter-relationship amongst all of the selected objective parameter values;

wherein the computer program product includes one or more lookup tables of values of attributes contributing to visual appeal embodied on said computer usable medium, and wherein the computer program product further includes computer readable code within said computer usable medium for, in the step of determining, indexing said lookup tables using the selected at least three objective parameter values to retrieve the derived values of attributes contributing to visual appeal;

establishing a rating value of the gemstone based upon said values of attributes contributing to visual appeal; and providing to the user an assessment of the aesthetic characteristics of the gemstone relative to said predetermined consumer preferences based upon said rating value and/or said values of attributes contributing to visual appeal.

14. Computer program product of claim 13 including computer readable code within said computer usable medium for applying an adjustment to one or more of the values of attributes contributing to visual appeal and/or the rating value in accordance with one or more of the following:
  (i) vertical spread;
  (ii) table size;
  (iii) girdle thickness;
  (iv) culet size;
  (v) half facets;
  (vi) symmetry;
  (vii) polish.

15. Computer program product of claim 13 including computer readable code within said computer usable medium for providing the user with a description of the visual appearance of the gemstone based upon the determined values of the attributes contributing to visual appeal and/or the established rating value.

16. Computer program product according to claim 13 wherein the gemstone is a diamond.

17. Computer program product of claim 13 wherein entries in the lookup tables are predetermined values computed using a computer software program for performing virtual diamond analysis.

18. Computer program product of claim 13 wherein entries in the lookup tables are predetermined values obtained by analyzing actual diamonds.

19. Computer program product of claim 13 including computer readable code within said computer usable medium for, in the step of determining, performing a virtual diamond analysis to compute said values of attributes contributing to visual appeal from a virtual model of a diamond corresponding with the received objective parameter values.

20. Computer program product of claim 13 including computer readable code within said computer usable medium for establishing said rating value by summing the values of attributes contributing to visual appeal.

21. A system for providing a user with an assessment of a gemstone having a cut shape, the system including:

input means for receiving at least three objective parameter values from the user relating to measured physical proportions of the gemstone, said values selected from the group comprising depth percentage, table percentage, crown angle, crown percentage, pavilion angle, pavilion percentage, culet percentage, girdle thickness, or other analogous physical proportion parameters applicable to the cut shape of the gemstone;

means for determining values for a plurality of attributes of the gemstone contributing to visual appeal, including one or more of the following: brilliance, fire, scintillation, and diameter spread;

the determining means being configured to determine each said attribute value by:
  selecting at least three of the received objective parameter values; and
  combining the selected objective parameter values to determine the said attribute value on the basis of predetermined consumer preferences that have been established taking into account the effect, upon the corresponding attribute contributing to visual appeal, of an inter-relationship amongst all of the selected objective parameter values;

wherein the determining means includes a means for retrieving said values of attributes contributing to visual appeal from one or more lookup tables indexed by the selected at least three objective parameter values;

means for establishing a rating value of the gemstone based upon said values of attributes contributing to visual appeal; and output means for providing to the user an assessment of the aesthetic characteristics of the relative to said predetermined consumer preferences based upon said computed rating value and/or said values of attributes contributing to visual appeal.

22. System of claim 21 wherein the input means comprises a computer input device for the user to enter said plurality of objective parameter values, and the output means comprises a computer display device for displaying the gem stone assessment to the user.

23. System of claim 21 wherein the input means and output means include means for receiving the objective parameter values from the user and for transmitting the gemstone assessment to the user over the internet.

24. System of claim 21 wherein the input means includes an interface with a diamond proportion measuring device for receiving proportional parameters of a diamond measured by said measuring device.

* * * * *

UNITED STATES PATENT AND TRADEMARK OFFICE
CERTIFICATE OF CORRECTION

PATENT NO. : 7,251,619 B2
APPLICATION NO. : 09/883561
DATED : July 31, 2007
INVENTOR(S) : Garry Ian Holloway It is certified that error appears in the above-identified patent and that said Letters Patent is hereby corrected as shown below:

Column 1, line 42, after "the" insert --erroneous idea that there is a single "ideal cut". Hence, Tolkowsky's proportions--.

Column 6, line 63, delete "390" and substitute therefor --39°--.

Claim 21, column 12, line 61, before "relative" insert --gemstone--.

Claim 22, column 13, line 2, delete "gem stone" and substitute therefor --gemstone--.

Signed and Sealed this

Sixteenth Day of October, 2007

JON W. DUDAS
*Director of the United States Patent and Trademark Office*